(12) United States Patent
Kania et al.

(10) Patent No.: US 9,267,178 B2
(45) Date of Patent: Feb. 23, 2016

(54) DETECTION AND DIFFERENTIATION OF DEMODEX MITES

(71) Applicant: University of Tennessee Research Foundation, Knoxville, TN (US)

(72) Inventors: Stephen A. Kania, Powell, TN (US); Linda A. Frank, Powell, TN (US)

(73) Assignee: UNIVERSITY OF TENNESSEE RESEARCH FOUNDATION, Knoxville, TN (US)

( * ) Notice: Subject to any disclaimer, the term of this patent is extended or adjusted under 35 U.S.C. 154(b) by 172 days.

(21) Appl. No.: 14/038,950

(22) Filed: Sep. 27, 2013

(65) Prior Publication Data

US 2014/0087966 A1     Mar. 27, 2014

Related U.S. Application Data

(60) Provisional application No. 61/706,344, filed on Sep. 27, 2012.

(51) Int. Cl.
*C12Q 1/68*     (2006.01)
*C40B 30/04*     (2006.01)

(52) U.S. Cl.
CPC ............... *C12Q 1/6888* (2013.01); *C40B 30/04* (2013.01)

(58) Field of Classification Search
None
See application file for complete search history.

(56) References Cited

PUBLICATIONS

Ravera et al., "Development of a real-time PCR to detect Demodex canis DNA in different tissue samples," Parasitol. Res. 2011, 108:305-308.*

* cited by examiner

*Primary Examiner* — Samuel Woolwine
*Assistant Examiner* — Kaijiang Zhang
(74) *Attorney, Agent, or Firm* — Jason M. Pass; FisherBroyles, LLP

(57) ABSTRACT

Methods of detecting *D. gatoi* or *D. cati*, are disclosed. A sample suspected of containing a nucleic acid of *D. gatoi* or *D. cati* is screened for the presence or absence of that nucleic acid. The presence of the *D. gatoi* or *D. cati* nucleic acid indicates the presence of *D. gatoi* or *D. cati*. Determining whether the *D. gatoi* or *D. cati* nucleic acid is present in the sample can be accomplished by detecting hybridization between a *D. gatoi* or *D. cati* probe. Probes and primers for the detection of *D. gatoi* or *D. cati* are also disclosed. Disclosed are isolated nucleic acids that encode a *D. gatoi* or *D. cati* rRNA gene sequence. Kits and arrays that contain the disclosed probes and/or primers also are disclosed.

12 Claims, 4 Drawing Sheets

*Demodex gatoi* Real-time PCR

Samples were run in duplicate. A positive sample with a Ct values of approximately 35.4 is shown.

FIG. 4    *Demodex cati* Real-time PCR
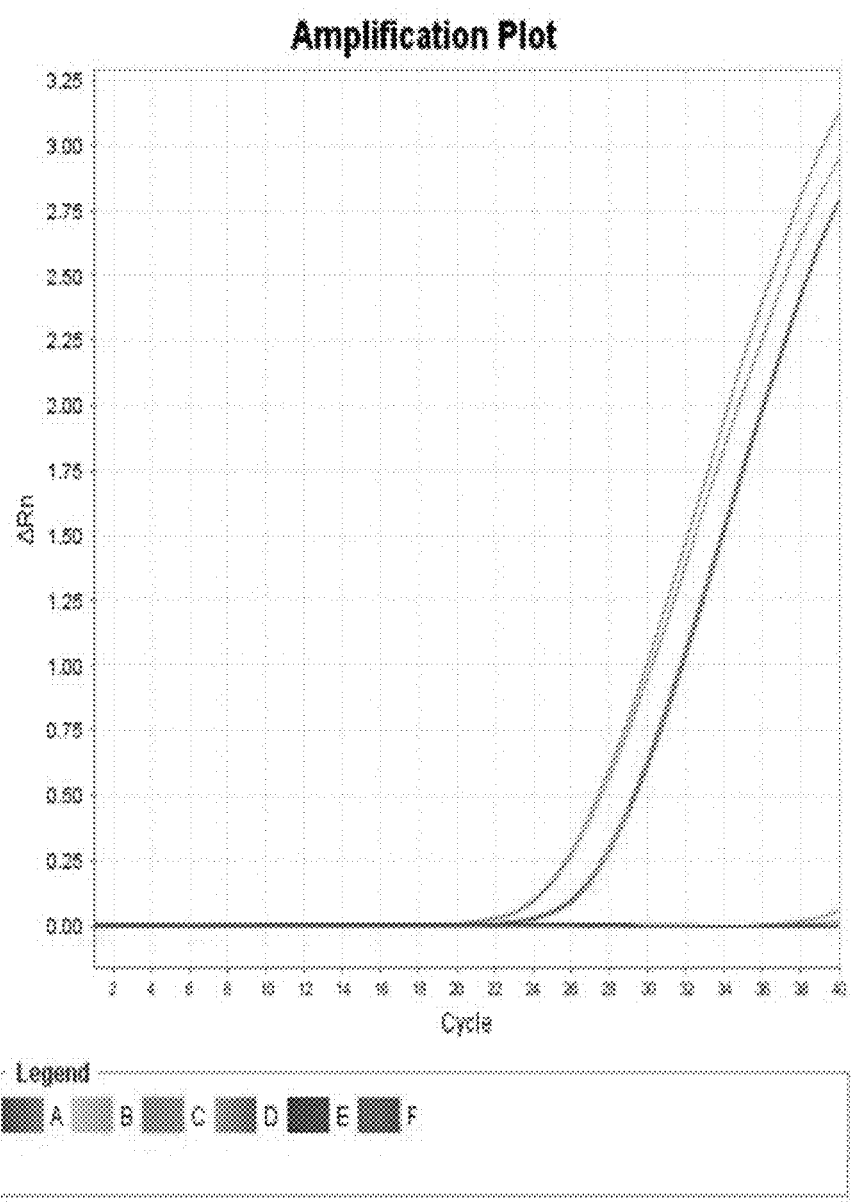
Samples were run in duplicate. Two positive samples are shown with Ct values of approximately 28.1 and 26.2.

DETECTION AND DIFFERENTIATION OF DEMODEX MITES

CROSS REFERENCE TO RELATED APPLICATION

This application claims the priority benefit of the early filing date of U.S. Provisional Application No. 61/706,344, filed Sep. 27, 2012, which is specifically incorporated herein in its entirety.

FIELD

This disclosure relates to primers and probes for detection and differentiation of demodex mites, as well as kits including the probes and primers and methods of using the probes and primers.

BACKGROUND

Feline demodicosis is a parasitic condition affecting the skin of cats. To date two species of mites have been described, *Demodex cati* and *Demodex gatoi*. A third unnamed species that differs morphologically from the others has also been observed. *Demodex cati* are considered normal fauna and are rarely associated with disease in cats with compromised immunity. Unlike *D. cati, D. gatoi* is believed to be a contagious parasite that can be transmitted among cats and possibly other species. Infestation with *D. gatoi* causes an extremely itchy (pruritic) skin disease in otherwise healthy cats. Diagnosis of *D. gatoi* requires the detection of mites, currently performed using a skin scraping technique. Because few mites may be needed for the development of clinical signs, this technique is insensitive and a negative result is uninterpretable. Therefore, a diagnosis may only be reached when cats' pruritus responds to treatment. This is problematic since the only effective treatment for *D. gatoi* infestation in cats is weekly dips with lime sulfur for a minimum of six weeks. It is recommended that all cats in a household be treated when *D. gatoi* is suspected. Because of the difficulty in diagnosing this disease with current technology and the difficulty and inconvenience of multiple cat dips, especially when diagnosis may be uncertain, a more sensitive and accurate test is highly desirable. Molecular methods of diagnosis, such as the polymerase chain reaction, have greatly improved diagnosis of infections. Molecular diagnostic approaches have not been possible for *D. gatoi* because no DNA sequence information has been available for feline mites.

Thus additional methods are need for the diagnosis of discrimination between *Demodex cati* and *Demodex gatoi*. This disclosure meets those needs.

SUMMARY

The present disclosure relates to methods of detecting the presence of *D. cati* and/or *D. gatoi* nucleic acids in a sample, such as a biological sample obtained from a subject, for example to detect *D. cati* and/or *D. gatoi* in the sample. The disclosed methods can be used for diagnosing an *D. cati* and/or *D. gatoi* infection, by analyzing a biological specimen from a subject to detect *D. cati* and/or *D. gatoi* nucleic acids, such as *D. cati* and/or *D. gatoi* ribosomal nucleic acids using the probes and/or primers disclosed herein. In addition, the probes and primers permit the rapid evaluation of a subject with an apparent *D. gatoi* infection by quickly determining whether the infection is caused by *D. gatoi* or another organism, such as *D. cati*. This rapid evaluation involves ruling out the presence of *D. gatoi*, ruling in the presence of *D. gatoi*, or a combination of both, for example in a multiplex real-time PCR assay.

In some embodiments, the method involves hybridizing a *D. gatoi* and/or *D. cati* nucleic acid to an *D. gatoi* and/or *D. cati* specific probe between 15 and 50 nucleotides in length, and detecting hybridization between *D. gatoi* and/or *D. cati* nucleic acid and the probe. In some embodiments, the probe is detectably labeled. In some embodiments, the probe is capable of hybridizing under conditions of very high stringency to a *D. gatoi* and/or *D. cati* nucleic acid sequence set forth as SEQ ID NO: 9 or SEQ ID NO: 10. In specific embodiments, the probe includes a nucleic acid sequence that is at least 95% identical to a nucleic acid sequence set forth as SEQ ID NO: 3 or SEQ ID NO: 6.

In some embodiments, the methods disclosed herein include amplifying the *D. gatoi* and/or *D. cati* nucleic acids with at least one primer specific for a *D. gatoi* and/or *D. cati* nucleic acid. In some embodiments, the primer specific for a *D. gatoi* and/or *D. cati* nucleic acid is 15 to 40 nucleotides in length and is capable of hybridizing under very high stringency conditions to a *D. gatoi* and/or *D. cati* nucleic acid sequence set forth as SEQ ID NO: 9 or SEQ ID NO: 10. In some embodiments, the primer specific for a *D. gatoi* or *D. cati* nucleic acid is 15 to 40 nucleotides in length and includes a nucleic acid sequence at least 95% identical to the nucleotide sequence set forth as SEQ ID NO: 1, SEQ ID NO: 2, SEQ ID NO: 4, or SEQ ID NO: 5.

This disclosure also relates to probes capable of hybridizing to *D. gatoi* or *D. cati* nucleic acids. In some embodiments, these probes are between 15 and 40 nucleotides in length and capable of hybridizing under very high stringency conditions to a *D. gatoi* and/or *D. cati* nucleic acid sequence set forth as SEQ ID NO: 9 or SEQ ID NO: 10. In several examples, these probes are between 15 and 40 nucleotides in length and include a nucleic acid sequence set forth as SEQ ID NO: 3, or SEQ ID NO: 6.

This disclosure also relates to primers capable of hybridizing to and amplifying *D. gatoi* and/or *D. cati* nucleic acids. In some embodiments, these primers are between 20 and 40 nucleotides in length and capable of hybridizing under very high stringency conditions to a *D. gatoi* and/or *D. cati* nucleic acid sequence set forth as SEQ ID NO: 9 or SEQ ID NO: 10. In several examples, these primers are 15 to 40 nucleotides in length and include a nucleic acid sequence at least 95% identical to a nucleic acid sequence set forth as SEQ ID NO: 1, SEQ ID NO: 2, SEQ ID NO: 4, or SEQ ID NO: 5.

The disclosure also provides devices, such as arrays, as well as kits for detecting *D. gatoi* and/or *D. cati* nucleic acids in a sample suspected of containing *D. gatoi* and/or *D. cati*.

Disclosed herein are isolated nucleic acids that encode the *D. gatoi* rRNA gene sequence. In some embodiments an isolated nucleic acids that encode the *D. gatoi* rRNA gene sequence includes the nucleic acid sequence set forth as SEQ ID NO: 9.

Disclosed herein are isolated nucleic acids that encode the *D. cati* rRNA gene sequence. In some embodiments an isolated nucleic acids that encode the *D. cati* rRNA gene sequence includes the nucleic acid sequence set forth as SEQ ID NO: 10.

The foregoing and other features, and advantages of the disclosure will become more apparent from the following detailed description, which proceeds with reference to the accompanying figures.

BRIEF DESCRIPTION OF THE DRAWINGS

FIG. 4 is a graph of *D. cati*, specific real-time PCR assay, showing the efficiency of the probe and primer sets.

SEQUENCE LISTING

Figure 1:
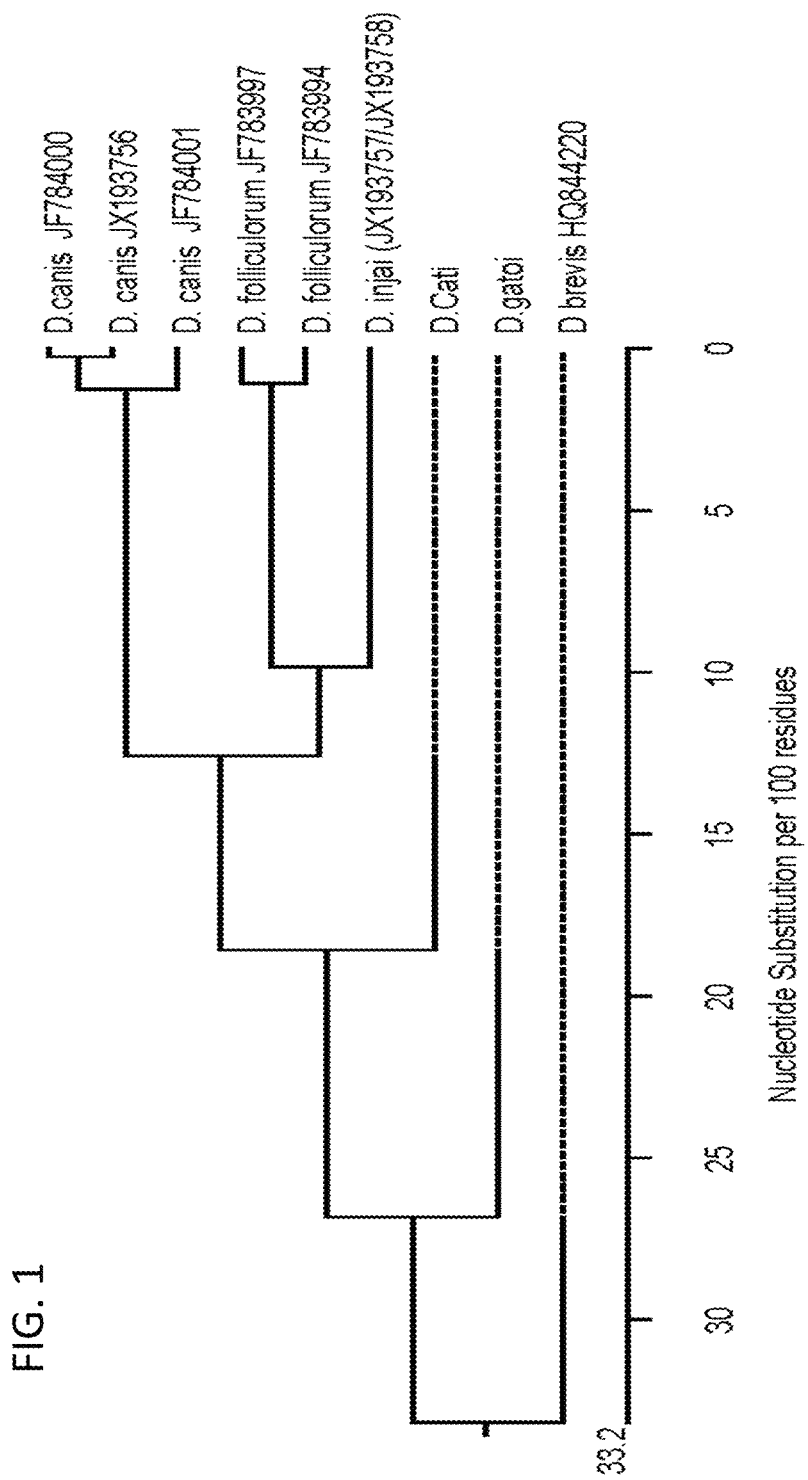
FIG. 1 is a phylogenetic tree showing the alignment of demodex rRNA gene sequences.

The nucleic and amino acid sequences listed in the accompanying sequence listing are shown using standard letter abbreviations for nucleotide bases, as defined in 37 C.F.R. §1.822. If only one strand of each nucleic acid sequence is shown, the complementary strand is understood as included by any reference to the displayed strand.

SEQ ID NOs: 1 and 2 are exemplary primers for *D. gatoi*.
SEQ ID NO: 3 is an exemplary probe for *D. gatoi*.
SEQ ID NOs: 4 and 5 are exemplary primers for *D. cati*.
SEQ ID NO: 6 is an exemplary probe for *D. cati*.
SEQ ID NOs: 7 and 8 are exemplary sequencing primers.
SEQ ID NOs: 9 is a partial sequence of a *D. gatoi* rRNA gene.
SEQ ID NOs: 10 is a partial sequence of a *D. cati* rRNA gene.

The Sequence Listing is submitted as an ASCII text file in the form of the file named UTK_0156_ST25.txt, which was created on Sep. 23, 2013, and is 4 kilobytes, which is incorporated by reference herein.

DETAILED DESCRIPTION

I. Explanation of Terms

Unless otherwise noted, technical terms are used according to conventional usage. Definitions of common terms in molecular biology may be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710) and other similar references.

As used herein, the singular forms "a," "an," and "the," refer to both the singular as well as plural, unless the context clearly indicates otherwise. For example, the term "a probe" includes single or plural probes and can be considered equivalent to the phrase "at least one probe."

As used herein, the term "comprises" means "includes." Thus, "comprising a probe" means "including a probe" without excluding other elements.

It is further to be understood that all base sizes or amino acid sizes, and all molecular weight or molecular mass values, given for nucleic acids or polypeptides are approximate, and are provided for descriptive purposes, unless otherwise indicated. Although many methods and materials similar or equivalent to those described herein can be used, particular suitable methods and materials are described below. In case of conflict, the present specification, including explanations of terms, will control. In addition, the materials, methods, and examples are illustrative only and not intended to be limiting.

To facilitate review of the various embodiments of the invention, the following explanations of terms are provided:

Animal: A living multi-cellular vertebrate or invertebrate organism, a category that includes, for example, mammals and birds. The term mammal includes domesticate animals, such as dogs and cats. Similarly, the term "subject" includes both human and veterinary subjects, such as dogs and cats.

Amplification: To increase the number of copies of a nucleic acid molecule. The resulting amplification products are called "amplicons." Amplification of a nucleic acid molecule (such as a DNA or RNA molecule) refers to use of a technique that increases the number of copies of a nucleic acid molecule in a sample, for example the number of copies of a *D. gatoi* or *D. cati* nucleic acid. An example of amplification is the polymerase chain reaction (PCR), in which a sample is contacted with a pair of oligonucleotide primers under conditions that allow for the hybridization of the primers to a nucleic acid template in the sample. The primers are extended under suitable conditions, dissociated from the template, re-annealed, extended, and dissociated to amplify the number of copies of the nucleic acid. This cycle can be repeated. The product of amplification can be characterized by such techniques as electrophoresis, restriction endonuclease cleavage patterns, oligonucleotide hybridization or ligation, and/or nucleic acid sequencing.

Other examples of in vitro amplification techniques include quantitative real-time PCR; reverse transcriptase PCR (RT-PCR); real-time PCR; real-time reverse transcriptase PCR (rt RT-PCR); nested PCR; strand displacement amplification (see U.S. Pat. No. 5,744,311); transcription-free isothermal amplification (see U.S. Pat. No. 6,033,881, repair chain reaction amplification (see WO 90/01069); ligase chain reaction amplification (see European patent publication EP-A-320 308); gap filling ligase chain reaction amplification (see U.S. Pat. No. 5,427,930); coupled ligase detection and PCR (see U.S. Pat. No. 6,027,889); and NASBA™ RNA transcription-free amplification (see U.S. Pat. No. 6,025,134) amongst others.

cDNA (complementary DNA): A piece of DNA lacking internal, non-coding segments (introns) and transcriptional regulatory sequences. cDNA also can contain untranslated regions (UTRs) that are responsible for translational control in the corresponding RNA molecule. cDNA can be synthesized in the laboratory by reverse transcription from RNA, for example an RNA from *D. gatoi* or *D. cati*, such as an RNA encoding *D. gatoi* or *D. cati* ribosomal RNA.

Change: To become different in some way, for example to be altered, such as increased or decreased. A detectable change is one that can be detected, such as a change in the intensity, frequency or presence of an electromagnetic signal, such as fluorescence, for example a change in fluorescence of a probe, such as an TAQMAN® probe specific for an *D. gatoi* or *D. cati* nucleic acid, such as a *D. gatoi* or *D. cati* ribosomal nucleic acid (for example a ribosomal RNA or an DNA encoding a ribosomal RNA, such as a genomic sequence and/or a cDNA sequence). In some examples, the detectable change is a reduction in fluorescence intensity. In some examples, the detectable change is an increase in fluorescence intensity.

Complementary: A double-stranded DNA or RNA strand consists of two complementary strands of base pairs. Complementary binding occurs when the base of one nucleic acid molecule forms a hydrogen bond to the base of another nucleic acid molecule. Normally, the base adenine (A) is complementary to thymidine (T) and uracil (U), while cytosine (C) is complementary to guanine (G). For example, the sequence 5'-ATCG-3' of one ssDNA molecule can bond to 3'-TAGC-5' of another ssDNA to form a dsDNA. In this example, the sequence 5'-ATCG-3' is the reverse complement of 3'-TAGC-5'.

Nucleic acid molecules can be complementary to each other even without complete hydrogen-bonding of all bases of each molecule. For example, hybridization with a complementary nucleic acid sequence can occur under conditions of differing stringency in which a complement will bind at some but not all nucleotide positions. In some examples, a nucleic acid molecule, such as the probes and primers specific for *D. gatoi* or *D. cati* nucleic acids disclosed herein, are complementary to a *D. gatoi* or *D. cati* ribosomal nucleic acid molecule or the amplification products of such a nucleic acid molecule.

Detect: To determine if an agent (such as a signal, particular nucleotide, amino acid, nucleic acid molecule, and/or organism) is present or absent, for example *D. gatoi* and/or *D. cati*. In some examples, this can further include quantification. For example, use of the disclosed probes in particular examples permits detection of a fluorophore, for example, detection of a signal from a fluorophore, which can be used to determine if a nucleic acid corresponding to nucleic acid of *D. gatoi* and/or *D. cati* is present. The detection of a *D. gatoi* and/or *D. cati* nucleic acid molecule indicates the presence of *D. gatoi* and/or *D. cati* in the sample, for example a *D. gatoi* and/or *D. cati* infection.

Electromagnetic radiation: A series of electromagnetic waves that are propagated by simultaneous periodic variations of electric and magnetic field intensity, and that includes radio waves, infrared, visible light, ultraviolet light, X-rays and gamma rays. In particular examples, electromagnetic radiation is emitted by a laser, which can possess properties of monochromaticity, directionality, coherence, polarization, and intensity. Lasers are capable of emitting light at a particular wavelength (or across a relatively narrow range of wavelengths), for example, so that energy from the laser can excite a donor but not an acceptor fluorophore.

Emission or emission signal: The light of a particular wavelength generated from a source. In particular examples, an emission signal is emitted from a fluorophore after the fluorophore absorbs light at its excitation wavelength(s).

Excitation or excitation signal: The light of a particular wavelength necessary and/or sufficient to excite an electron transition to a higher energy level. In particular examples, an excitation is the light of a particular wavelength necessary and/or sufficient to excite a fluorophore to a state such that the fluorophore will emit a different (such as a longer) wavelength of light then the wavelength of light from the excitation signal.

Fluorophore: A chemical compound, which when excited by exposure to a particular stimulus such as a defined wavelength of light, emits light (fluoresces), for example at a different wavelength (such as a longer wavelength of light).

Fluorophores are part of the larger class of luminescent compounds. Luminescent compounds include chemiluminescent molecules, which do not require a particular wavelength of light to luminesce, but rather use a chemical source of energy. Therefore, the use of chemiluminescent molecules (such as aequorin) eliminates the need for an external source of electromagnetic radiation, such as a laser.

Examples of particular fluorophores that can be used in the *D. gatoi* and/or *D. cati* specific probes and primers disclosed herein are known to those of skill in the art and include those provided in U.S. Pat. No. 5,866,366 to Nazarenko et al., such as 4-acetamido-4'-isothiocyanatostilbene-2,2'disulfonic acid; acridine and derivatives such as acridine and acridine isothiocyanate, 5-(2'-aminoethyl)aminonaphthalene-1-sulfonic acid (EDANS), 4-amino-N-[3-vinylsulfonyl)phenyl] naphthalimide-3,5 disulfonate (Lucifer Yellow VS), N-(4-anilino-1-naphthyl)maleimide, anthranilamide; Brilliant Yellow; coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino] naphthalene-1-sulfonyl chloride (DNS, dansyl chloride); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6-dichlorotriazin-2-yl)aminofluorescein (DTAF), 2'7'-dimethoxy-4'5'-dichloro-6-carboxyfluorescein (JOE), fluorescein, fluorescein isothiocyanate (FITC), QFITC (XRITC), -6-carboxy-fluorescein (HEX), and TET (Tetramethyl fluorescein); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (CIBACRON™. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, N,N,N',N'-tetramethyl-6-carboxyrhodamine (TAMRA), tetramethyl rhodamine, and tetramethyl rhodamine isothiocyanate (TRITC); sulforhodamine B; sulforhodamine 101 and sulfonyl chloride derivative of sulforhodamine 101 (Texas Red); riboflavin; rosolic acid and terbium chelate derivatives; LightCycler Red 640; Cy5.5; and Cy56-carboxyfluorescein; boron dipyrromethene difluoride (BODIPY); acridine; stilbene; 6-carboxy-X-rhodamine (ROX); Texas Red; Cy3; Cy5, VIC® (Applied Biosystems); LC Red 640; LC Red 705; and Yakima yellow amongst others.

Other suitable fluorophores include those known to those skilled in the art, for example those available from Molecular Probes (Eugene, Oreg.). In particular examples, a fluorophore is used as a donor fluorophore or as an acceptor fluorophore.

"Acceptor fluorophores" are fluorophores which absorb energy from a donor fluorophore, for example in the range of about 400 to 900 nm (such as in the range of about 500 to 800 nm). Acceptor fluorophores generally absorb light at a wavelength which is usually at least 10 nm higher (such as at least 20 nm higher) than the maximum absorbance wavelength of the donor fluorophore, and have a fluorescence emission maximum at a wavelength ranging from about 400 to 900 nm. Acceptor fluorophores have an excitation spectrum that overlaps with the emission of the donor fluorophore, such that energy emitted by the donor can excite the acceptor. Ideally, an acceptor fluorophore is capable of being attached to a nucleic acid molecule.

In a particular example, an acceptor fluorophore is a dark quencher, such as Dabcyl, QSY7 (Molecular Probes), QSY33 (Molecular Probes), BLACK HOLE QUENCHERS™ (Glen Research), ECLIPSE™ Dark Quencher (Epoch Biosciences), or IOWA BLACK™ (Integrated DNA Technologies). A quencher can reduce or quench the emission of a donor fluorophore. In such an example, instead of detecting an increase in emission signal from the acceptor fluorophore when in sufficient proximity to the donor fluorophore (or detecting a decrease in emission signal from the acceptor fluorophore when a significant distance from the donor fluorophore), an increase in the emission signal from the donor fluorophore can be detected when the quencher is a significant distance from the donor fluorophore (or a decrease in emission signal from the donor fluorophore when in sufficient proximity to the quencher acceptor fluorophore).

"Donor Fluorophores" are fluorophores or luminescent molecules capable of transferring energy to an acceptor fluorophore, thereby generating a detectable fluorescent signal from the acceptor. Donor fluorophores are generally compounds that absorb in the range of about 300 to 900 nm, for example about 350 to 800 nm. Donor fluorophores have a strong molar absorbance coefficient at the desired excitation wavelength, for example greater than about $10^3$ $M^{-1}$ $cm^{-1}$.

Fluorescence Resonance Energy Transfer (FRET): A spectroscopic process by which energy is passed between an initially excited donor to an acceptor molecule separated by 10-100 Å. The donor molecules typically emit at shorter wavelengths that overlap with the absorption of the acceptor molecule. The efficiency of energy transfer is proportional to the inverse sixth power of the distance (R) between the donor and acceptor ($1/R^6$) fluorophores and occurs without emission of a photon. In applications using FRET, the donor and acceptor dyes are different, in which case FRET can be detected either by the appearance of sensitized fluorescence of the acceptor or by quenching of donor fluorescence. For example, if the donor's fluorescence is quenched it indicates the donor and acceptor molecules are within the Förster radius (the distance where FRET has 50% efficiency, about 20-60 Å), whereas if the donor fluoresces at its characteristic wavelength, it denotes that the distance between the donor and acceptor molecules has increased beyond the Förster radius, such as when a TAQMAN® probe is degraded by Taq polymerase following hybridization of the probe to a target nucleic acid sequence or when a hairpin probe is hybridized to a target nucleic acid sequence. In another example, energy is transferred via FRET between two different fluorophores such that the acceptor molecule can emit light at its characteristic wavelength, which is always longer than the emission wavelength of the donor molecule.

Examples of oligonucleotides using FRET that can be used to detect amplicons include linear oligoprobes, such as Hyb-Probes, 5' nuclease oligoprobes, such as TAQMAN® probes, hairpin oligoprobes, such as molecular beacons, scorpion primers and UniPrimers, minor groove binding probes, and self-fluorescing amplicons, such as sunrise primers.

Hybridization: The ability of complementary single-stranded DNA or RNA to form a duplex molecule (also referred to as a hybridization complex). Nucleic acid hybridization techniques can be used to form hybridization complexes between a probe or primer and a nucleic acid, such as a D. gatoi and/or D. cati nucleic acid molecule, such as a D. gatoi and/or D. cati ribosomal nucleic acid molecule. For example, a probe or primer (such as any of SEQ ID NOs: 1-6) having some homology to a D. gatoi and/or D. cati nucleic acid molecule will form a hybridization complex with a D. gatoi and/or D. cati nucleic acid molecule (such as any of SEQ ID NOs: 9 or 10).

Hybridization conditions resulting in particular degrees of stringency will vary depending upon the nature of the hybridization method and the composition and length of the hybridizing nucleic acid sequences. Generally, the temperature of hybridization and the ionic strength (such as the Na+ concentration) of the hybridization buffer will determine the stringency of hybridization. Calculations regarding hybridization conditions for attaining particular degrees of stringency are discussed in Sambrook et al., (1989) Molecular Cloning, second edition, Cold Spring Harbor Laboratory, Plainview, N.Y. (chapters 9 and 11).

Isolated: An "isolated" biological component (such as a nucleic acid) has been substantially separated or purified away from other biological components in which the component naturally occurs, such as other chromosomal and extra-chromosomal DNA, RNA, and proteins, such as isolated D. gatoi and/or D. cati nucleic acid molecules, for example ribosomal nucleic acids. Nucleic acids that have been "isolated" include nucleic acids purified by standard purification methods. The term also embraces nucleic acids prepared by recombinant expression in a host cell as well as chemically synthesized nucleic acids, such as probes and primers, for example D. gatoi and/or D. cati specific probes and primers disclosed herein. Isolated does not require absolute purity, and can include nucleic acid molecules that are at least 50% isolated, such as at least 75%, 80%, 90%, 95%, 98%, 99%, or even 100% isolated.

Label: An agent capable of detection, for example by spectrophotometry, flow cytometry, or microscopy. For example, a label can be attached to a nucleotide, thereby permitting detection of the nucleotide, such as detection of the nucleic acid molecule of which the nucleotide is a part, such as a D. gatoi and/or D. cati specific probe and/or primer. Examples of labels include, but are not limited to, radioactive isotopes, enzyme substrates, co-factors, ligands, chemiluminescent agents, fluorophores, haptens, enzymes, and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Nucleic acid (molecule or sequence): A deoxyribonucleotide or ribonucleotide polymer including without limitation, cDNA, mRNA, genomic DNA, and synthetic (such as chemically synthesized) DNA or RNA. The nucleic acid can be double stranded (ds) or single stranded (ss). Where single stranded, the nucleic acid can be the sense strand or the antisense strand. Nucleic acids can include natural nucleotides (such as A, T/U, C, and G), and can include analogs of natural nucleotides, such as labeled nucleotides. In some examples, a nucleic acid is a D. gatoi and/or D. cati nucleic acid, which can include nucleic acids purified from D. gatoi and/or D. cati as well as the amplification products of such nucleic acids.

Nucleotide: The fundamental unit of nucleic acid molecules. A nucleotide includes a nitrogen-containing base attached to a pentose monosaccharide with one, two, or three phosphate groups attached by ester linkages to the saccharide moiety.

The major nucleotides of DNA are deoxyadenosine 5'-triphosphate (dATP or A), deoxyguanosine 5'-triphosphate (dGTP or G), deoxycytidine 5'-triphosphate (dCTP or C) and deoxythymidine 5'-triphosphate (dTTP or T). The major nucleotides of RNA are adenosine 5'-triphosphate (ATP or A), guanosine 5'-triphosphate (GTP or G), cytidine 5'-triphosphate (CTP or C) and uridine 5'-triphosphate (UTP or U).

Nucleotides include those nucleotides containing modified bases, modified sugar moieties and modified phosphate backbones, for example as described in U.S. Pat. No. 5,866,336 to Nazarenko et al. (herein incorporated by reference).

Examples of modified base moieties which can be used to modify nucleotides at any position on its structure include, but are not limited to: 5-fluorouracil, 5-bromouracil, 5-chlorouracil, 5-iodouracil, hypoxanthine, xanthine, acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N~6-sopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, methoxyarninomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid, pseudouracil, queosine, 2-thiocytosine, 5-methyl-2-thiouracil, 2-thiouracil, 4-thiouracil, 5-methyluracil, uracil-5-oxyacetic acid methylester, uracil-S-oxyacetic acid, 5-methyl-2-thiouracil, 3-(3-amino-3-N-2-carboxypropyl) uracil, and 2,6-diaminopurine amongst others.

Examples of modified sugar moieties, which may be used to modify nucleotides at any position on its structure, include, but are not limited to arabinose, 2-fluoroarabinose, xylose, and hexose, or a modified component of the phosphate backbone, such as phosphorothioate, a phosphorodithioate, a phosphoramidothioate, a phosphoramidate, a phosphordiamidate, a methylphosphonate, an alkyl phosphotriester, or a formacetal or analog thereof.

Primers: Short nucleic acid molecules, such as a DNA oligonucleotide, for example sequences of at least 15 nucleotides, which can be annealed to a complementary target nucleic acid molecule by nucleic acid hybridization to form a hybrid between the primer and the target nucleic acid strand. A primer can be extended along the target nucleic acid molecule by a polymerase enzyme. Therefore, primers can be used to amplify a target nucleic acid molecule (such as a portion of a *D. gatoi* and/or *D. cati* nucleic acid molecule, for example a portion of a *D. gatoi* and/or *D. cati* ribosomal nucleic acid molecule), wherein the sequence of the primer is specific for the target nucleic acid molecule, for example so that the primer will hybridize to the target nucleic acid molecule under very high stringency hybridization conditions.

The specificity of a primer increases with its length. Thus, for example, a primer that includes 30 consecutive nucleotides will anneal to a target sequence with a higher specificity than a corresponding primer of only 15 nucleotides. Thus, to obtain greater specificity, probes and primers can be selected that include at least 15, 20, 25, 30, 35, 40, 45, 50 or more consecutive nucleotides.

In particular examples, a primer is at least 15 nucleotides in length, such as at least 15 contiguous nucleotides complementary to a target nucleic acid molecule. Particular lengths of primers that can be used to practice the methods of the present disclosure (for example, to amplify a region of a *D. gatoi* and/or *D. cati* nucleic acid molecule) include primers having at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, or more contiguous nucleotides complementary to the target nucleic acid molecule to be amplified, such as a primer of 15-60 nucleotides, 15-50 nucleotides, or 15-30 nucleotides.

Primer pairs can be used for amplification of a nucleic acid sequence, for example, by PCR, real-time PCR, or other nucleic-acid amplification methods known in the art. An "upstream" or "forward" primer is a primer 5' to a reference point on a nucleic acid sequence. A "downstream" or "reverse" primer is a primer 3' to a reference point on a nucleic acid sequence. In general, at least one forward and one reverse primer are included in an amplification reaction. PCR primer pairs can be derived from a known sequence (such as the *D. gatoi* and/or *D. cati* nucleic acid sequences set forth as SEQ ID NOs: 9 or 10), for example, by using computer programs intended for that purpose such as Primer (Version 0.5, © 1991, Whitehead Institute for Biomedical Research, Cambridge, Mass.) or PRIMER EXPRESS® Software (Applied Biosystems, AB, Foster City, Calif.).

Methods for preparing and using primers are described in, for example, Sambrook et al. (1989) *Molecular Cloning: A Laboratory Manual*, Cold Spring Harbor, N.Y.; Ausubel et al. (1987) *Current Protocols in Molecular Biology*, Greene Publ. Assoc. & Wiley-Intersciences. In one example, a primer includes a label.

Probe: A probe comprises an isolated nucleic acid capable of hybridizing to a target nucleic acid (such as a *D. gatoi* and/or *D. cati* nucleic acid, for example a *D. gatoi* and/or *D. cati* ribosomal nucleic acid molecule). A detectable label or reporter molecule can be attached to a probe. Typical labels include radioactive isotopes, enzyme substrates, co-factors, ligands, chemiluminescent or fluorescent agents, haptens, and enzymes.

Methods for labeling and guidance in the choice of labels appropriate for various purposes are discussed, for example, in Sambrook et al., *Molecular Cloning: A Laboratory Manual*, Cold Spring Harbor Laboratory Press (1989) and Ausubel et al., *Current Protocols in Molecular Biology*, Greene Publishing Associates and Wiley-Intersciences (1987).

In a particular example, a probe includes at least one fluorophore, such as an acceptor fluorophore or donor fluorophore. For example, a fluorophore can be attached at the 5'- or 3'-end of the probe or even internal to the probe. In specific examples, the fluorophore is attached to the base at the 5'-end of the probe, the base at its 3'-end, the phosphate group at its 5'-end or a modified base, such as a T internal to the probe.

Probes are generally at least 15 nucleotides in length, such as at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50 at least 51, at least 52, at least 53, at least 54, at least 55, at least 56, at least 57, at least 58, at least 59, at least 60, or more contiguous nucleotides complementary to the target nucleic acid molecule, such as 15-60 nucleotides, 15-50 nucleotides, 15-40 nucleotides, or 15-30 nucleotides.

Polymerizing agent: A compound capable of reacting monomer molecules (such as nucleotides) together in a chemical reaction to form linear chains or a three-dimensional network of polymer chains. A particular example of a polymerizing agent is polymerase, an enzyme which catalyzes the 5' to 3' elongation of a primer strand complementary to a nucleic acid template. Examples of polymerases that can be used to amplify a nucleic acid molecule include, but are not limited to the *E. coli* DNA polymerase I, specifically the Klenow fragment which has 3' to 5' exonuclease activity, Taq polymerase, reverse transcriptase (such as HIV-1 RT), *E. coli* RNA polymerase, and wheat germ RNA polymerase II.

The choice of polymerase is dependent on the nucleic acid to be amplified. If the template is a single-stranded DNA molecule, a DNA-directed DNA or RNA polymerase can be used; if the template is a single-stranded RNA molecule, then a reverse transcriptase (such as an RNA-directed DNA polymerase) can be used.

Quantitating a nucleic acid molecule: Determining or measuring a quantity (such as a relative quantity) of nucleic acid molecules present, such as the number of amplicons or the number of nucleic acid molecules present in a sample. In particular examples, it is determining the relative amount or actual number of nucleic acid molecules present in a sample, such as *D. gatoi* and/or *D. cati* nucleic acid molecules present in a sample.

Quenching of fluorescence: A reduction of fluorescence. For example, quenching of a fluorophore's fluorescence occurs when a quencher molecule (such as the fluorescence quenchers listed above) is present in sufficient proximity to the fluorophore that it reduces the fluorescence signal (for example, prior to the binding of a probe to an *D. gatoi* and/or *D. cati* nucleic acid sequence, when the probe contains a fluorophore and a quencher).

Real-time PCR: A method for detecting and measuring products generated during each cycle of a PCR, which are proportionate to the amount of template nucleic acid prior to the start of PCR. The information obtained, such as an amplification curve, can be used to determine the presence of a target nucleic acid (such as a *D. gatoi* and/or *D. cati* nucleic acid) and/or quantitate the initial amounts of a target nucleic acid sequence. Exemplary procedures for real-time PCR can be found in "Quantitation of DNA/RNA Using Real-Time PCR Detection" published by Perkin Elmer Applied Biosystems (1999) and to PCR Protocols (Academic Press New York, 1989).

In some examples, the amount of amplified target nucleic acid (such as a *D. gatoi* and/or *D. cati* nucleic acid molecule for example a *D. gatoi* and/or *D. cati* ribosomal nucleic acid molecule) is detected using a labeled probe, such as a probe labeled with a fluorophore, for example a TAQMAN® probe. In this example, the increase in fluorescence emission is measured in real-time, during the course of the real-time PCR. This increase in fluorescence emission is directly related to the increase in target nucleic acid amplification (such as *D. gatoi* and/or *D. cati* nucleic acid amplification). In some examples, the change in fluorescence (dRn) is calculated using the equation $dRn=Rn^+ - Rn^-$, with $Rn^+$ being the fluorescence emission of the product at each time point and $Rn^-$ being the fluorescence emission of the baseline. The dRn values are plotted against cycle number, resulting in amplification plots for each sample, the threshold value ($C_t$) is the PCR cycle number at which the fluorescence emission (dRn) exceeds a chosen threshold, which is typically 10 times the standard deviation of the baseline (this threshold level can, however, be changed if desired).

The threshold cycle is when the system begins to detect the increase in the signal associated with an exponential growth of PCR product during the log-linear phase. This phase provides information about the reaction. The slope of the log-linear phase is a reflection of the amplification efficiency. The efficiency of the reaction can be calculated by the following equation: $E=10^{(-1/slope)}-1$. The efficiency of the PCR should be 90-100% meaning doubling of the amplicon at each cycle. This corresponds to a slope of −3.1 to −3.6 in the $C_t$ vs. log-template amount standard curve. In order to obtain accurate and reproducible results, reactions should have efficiency as close to 100% as possible (meaning a two-fold increase of amplicon at each cycle).

Sample: A sample, such as a biological sample, is a sample obtained from a plant or animal subject. As used herein, biological samples include all clinical samples useful for detection *D. gatoi* and/or *D. cati* infection in subjects, such as a veterinary subject including, but not limited to, cells, tissues; biopsied or surgically removed tissue, including tissues that are, for example, unfixed, frozen, fixed in formalin and/or embedded in paraffin; skin scrapes; surface washings and the like.

Sequence identity/similarity: The identity/similarity between two or more nucleic acid sequences, or two or more amino acid sequences, is expressed in terms of the identity or similarity between the sequences. Sequence identity can be measured in terms of percentage identity; the higher the percentage, the more identical the sequences are. Homologs or orthologs of nucleic acid or amino acid sequences possess a relatively high degree of sequence identity/similarity when aligned using standard methods.

Methods of alignment of sequences for comparison are well known in the art. Various programs and alignment algorithms are described in: Smith & Waterman, *Adv. Appl. Math.* 2:482, 1981; Needleman & Wunsch, *J. Mol. Biol.* 48:443, 1970; Pearson & Lipman, *Proc. Natl. Acad. Sci. USA* 85:2444, 1988; Higgins & Sharp, *Gene,* 73:237-44, 1988; Higgins & Sharp, CABIOS 5:151-3, 1989; Corpet et al., *Nuc. Acids Res.* 16:10881-90, 1988; Huang et al. *Computer Appls. in the Biosciences* 8, 155-65, 1992; and Pearson et al., *Meth. Mol. Bio.* 24:307-31, 1994. Altschul et al., *J. Mol. Biol.* 215: 403-10, 1990, presents a detailed consideration of sequence alignment methods and homology calculations.

The NCBI Basic Local Alignment Search Tool (BLAST) (Altschul et al., *J. Mol. Biol.* 215:403-10, 1990) is available from several sources, including the National Center for Biological Information (NCBI, National Library of Medicine, Building 38A, Room 8N805, Bethesda, Md. 20894) and on the Internet, for use in connection with the sequence analysis programs blastp, blastn, blastx, tblastn, and tblastx. Blastn is used to compare nucleic acid sequences, while blastp is used to compare amino acid sequences. Additional information can be found at the NCBI web site.

Once aligned, the number of matches is determined by counting the number of positions where an identical nucleotide or amino acid residue is present in both sequences. The percent sequence identity is determined by dividing the number of matches either by the length of the sequence set forth in the identified sequence, or by an articulated length (such as 100 consecutive nucleotides or amino acid residues from a sequence set forth in an identified sequence), followed by multiplying the resulting value by 100. For example, a nucleic acid sequence that has 1166 matches when aligned with a test sequence having 1554 nucleotides is 75.0 percent identical to the test sequence (1166÷1554*100=75.0). The percent sequence identity value is rounded to the nearest tenth. For example, 75.11, 75.12, 75.13, and 75.14 are rounded down to 75.1, while 75.15, 75.16, 75.17, 75.18, and 75.19 are rounded up to 75.2. The length value will always be an integer. In another example, a target sequence containing a 20-nucleotide region that aligns with 20 consecutive nucleotides from an identified sequence as follows contains a region that shares 75 percent sequence identity to that One indication that two nucleic acid molecules are closely related is that the two molecules hybridize to each other under stringent conditions. Stringent conditions are sequence-dependent and are different under different environmental parameters.

The nucleic acid probes and primers disclosed herein are not limited to the exact sequences shown, as those skilled in the art will appreciate that changes can be made to a sequence, and not substantially affect the ability of the probe or primer to function as desired. For example, sequences having at least 80%, at least 90%, at least 95%, at least 96%, at least 97%, at least 98%, or at least 99%, such as 100% sequence identity to any of SEQ ID NOs: 1-6 are provided herein. One of skill in the art will appreciate that these sequence identity ranges are provided for guidance only; it is possible that probes and primer can be used that fall outside these ranges.

Signal: A detectable change or impulse in a physical property that provides information. In the context of the disclosed methods, examples include electromagnetic signals such as light, for example light of a particular quantity or wavelength. In certain examples, the signal is the disappearance of a physical event, such as quenching of light.

TAQMAN® PCR: A TAQMAN® probe that typically contains reporter (such as a short-wavelength fluorophore, for example 6-carboxyfluorescein (FAM)) and quencher (such as a long-wavelength fluorophore, for example BLACKHOLE QUENCHER™ 1 (BHQ™ 1)) is selected to bind to one strand of a target nucleic acid. When irradiated energy is transferred (via FRET) from the reporter to the quencher on the other end of the intact TAQMAN® probe. Thus, the close proximity of the reporter and the quencher prevents detection of any signal while the TAQMAN® probe is intact. When Taq polymerase replicates the target nucleic acid using primers on which a TAQMAN® probe is bound, the polymerase's 5' exonuclease activity cleaves the TAQMAN® probe. Upon degradation, FRET is interrupted, ending the activity of the quencher. The reporter starts to emit signal, which increases in each cycle proportional to the rate of the TAQMAN® probe cleavage. Accumulation of PCR product is detected by monitoring the increase in signal of the reporter. Because the cleavage occurs only if the TAQMAN® probe hybridizes to a target nucleic acid, the origin of the detected fluorescence is specific amplification. The process of hybridization and cleavage does not interfere with the exponential accumulation of a PCR product.

Target nucleic acid molecule: A nucleic acid molecule whose detection, quantitation, qualitative detection, or a combination thereof, is intended. The nucleic acid molecule need not be in a purified form. Various other nucleic acid molecules can also be present with the target nucleic acid molecule. For example, the target nucleic acid molecule can be a specific nucleic acid molecule (which can include RNA or DNA such as *D. gatoi* and/or *D. cati* RNA, or DNA such as *D. gatoi* and/or *D. cati* ribosomal RNA or DNA), the amplification of which is intended. Purification or isolation of the target nucleic acid molecule, if needed, can be conducted by methods known to those in the art, such as by using a commercially available purification kit or the like. In one example, a target nucleic molecule is a *D. gatoi* and/or *D. cati* nucleic acid sequence.

II. Overview of Several Embodiments

Disclosed herein are methods for the detection and discrimination between *D. gatoi* and *D. cati*. The methods have been developed with a unique set of nucleic acid probes and/or primers that are surprisingly effective at detecting and discriminating between *D. gatoi* and *D. cati* a variety of conditions. This ability to rapidly screen and identify a mite among these diverse groups is a significant veterinary health advantage. This assay can be used to test all pruritic cats to determine the etiology of their symptoms. It can also be used to screen all newly acquired cats to prevent the introduction of this contagious mite to uninfected cats.

As disclosed herein the inventors have isolated sequenced ribosomal RNA (rRNA) genes from the species of mites known to infect cats. This information was used to develop a probe based real-time (quantitative) PCR assay that specifically amplifies and detects one or both of *D. gatoi* and *D. cati* DNA.

Disclosed herein are isolated nucleic acids that encode the *D. gatoi* rRNA gene sequence. In some embodiments an isolated nucleic acids that encode the *D. gatoi* rRNA gene sequence includes the nucleic acid sequence set forth as, TACTGTGCTAAGGTAGCGAAGT-CATTTGTTTTTTTATTGGAAACTTGTATGA GGG-GATTTATGGAGTAGAT-TATTTGAAAATTTTATATTTAGGAATTTGATAT TTGGATGAAAATTTCTAATTTTTCT-TAAAGACGAGAAGACCCTAGAATCTTT ATTTTCAT-AATTAGGGTGAATTTTTATTTGGGG-GAAAGTTTTATATTTATAA AAAGATTTGTTATTTTGAACTTTTTAAG-GTTGGTAGGATAGATACTTTAGGG ATAACAG-GATAATTTTCTTTTGAAGTTCT-TATTTTGGAGGAAGTTTATTACCT CGATGTTGGCTTTTGAA (SEQ ID NO: 9).

Disclosed herein are isolated nucleic acids that encode the *D. cati* rRNA gene sequence. In some embodiments an isolated nucleic acids that encode the *D. cati* rRNA gene sequence includes the nucleic acid sequence set forth as, CTCYTGGGAAATAAGGAACTTCAAA-GAAAATAATCCTGTTAACCCCGAAGT ATCTATC-CAATCAACCTACAAAAGTTCCTCAT-AATAAAAATAAATATAAAA ATAAAACTTTCCCCCAAATAAAAAT-TAAAATACCTTTTTCTAAAATAAAGAT TTCGGGGTCTTCTCGTCTTTA-GAAATAATTCCAATTTTTCATGGAAAAATTA AAT-TCACCAATTAAAACATTCAT-AAAAAAATCTTCATTAATCCCCTCATACA AGTTTCCAATAAAAAAACAAATGACT-TCGCTACCTTAGCACAGT (SEQ ID NO: 10).

Probes and Primers

Probes capable of hybridizing to and detecting the presence of *D. gatoi* and/or *D. cati* nucleic acid molecules, such as *D. gatoi* and/or *D. cati* RNA, or DNA such as *D. gatoi* and/or *D. cati* ribosomal RNA or DNA nucleic acid molecules, are disclosed. In some embodiments, such probes are specific for *D. gatoi* or *D. cati*, in that they do not specifically hybridize to sequences from other organisms, such as other bacteria. The disclosed probes are between 15 and 50 nucleotides in length, such as 15. 16, 17, 18, 19, 20, 21, 22, 23, 24, 25, 26, 27, 28 29, 30, 31, 32, 33, 34, 35, 36, 37, 38, 39, 40, 41, 42, 43, 34, 35, 36, 37, 38, 39, or 50 nucleotides in length and are capable of hybridizing to the *D. gatoi* or *D. cati* nucleic acid molecule, such as set forth as SEQ ID NOs: 9 or 10 respectively.

In several embodiments, a probe capable of hybridizing to a *D. gatoi* nucleic molecule contains a nucleic acid sequence that is at least 95% identical, such as at least 96%, at least 97%, at least 98%, at least 99%, or even 100% identical, to the nucleotide sequence set forth as SEQ ID NO: 3 or the complement thereof. In several embodiments, a probe capable of hybridizing to a *D. gatoi* nucleic acid molecule consists essentially of a nucleic acid sequence set forth as SEQ ID NO: 3 or the complement thereof.

In several embodiments, a probe capable of hybridizing to a *D. gatoi* nucleic molecule contains a nucleic acid sequence that is at least 95% identical, such as at least 96%, at least 97%, at least 98%, at least 99%, or even 100% identical, to the nucleotide sequence set forth as SEQ ID NO: 6 or the complement thereof. In several embodiments, a probe capable of hybridizing to a *D. gatoi* nucleic acid molecule consists essentially of a nucleic acid sequence set forth as SEQ ID NO:6 or the complement thereof.

In some embodiments, the probe is detectably labeled, either with an isotopic or non-isotopic label, alternatively the target nucleic acid (such as a *D. gatoi* and/or *D. cati*) is labeled. Non-isotopic labels can include a fluorescent or luminescent molecule, biotin, an enzyme or enzyme substrate or a chemical. Such labels are preferentially chosen such that the hybridization of the probe with target nucleic acid (such as a *D. gatoi* and/or *D. cati* nucleic acid molecule or subsequence thereof) can be detected. In some examples, the probe is labeled with a fluorophore. Examples of suitable fluorophore labels are given above. In some examples, the fluorophore is a donor fluorophore. In other examples, the fluorophore is an accepter fluorophore, such as a fluorescence quencher. In some examples, the probe includes both a donor fluorophore and an accepter fluorophore, for example a donor fluorophore such as a FAM and an acceptor fluorophore such as a BLACK HOLE® quencher. Appropriate donor/acceptor fluorophore pairs can be selected using routine methods. In one example, the donor emission wavelength is one that can significantly excite the acceptor, thereby generating a detectable emission from the acceptor. In some examples, the probe is modified at the 3'-end to prevent extension of the probe by a polymerase.

Primers capable of hybridizing to and directing the amplification of a *D. gatoi* and/or *D. cati* nucleic acid molecule are disclosed. In some embodiments, such primers are specific for *D. gatoi* or *D. cati*, in that they do not specifically hybridize to nucleic acid sequences from other organisms, such as other bacteria. The primers disclosed herein are between 15 to 40 nucleotides in length, such as 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or even 50 nucleotides in length.

In several embodiments, a primer is capable of hybridizing under very high stringency conditions to a *D. gatoi* nucleic acid sequence, such as a sequence set forth as SEQ ID NO: 9, and directing the amplification of the *D. gatoi* nucleic acid molecule, for example amplification of SEQ ID NO: 9 or a subsequence thereof. In several embodiments, a primer is capable of hybridizing under very high stringency conditions to a *D. cati* nucleic acid sequence, such as a sequence set forth as SEQ ID NO: 10, and directing the amplification of the *D. cati* nucleic acid molecule, for example amplification of SEQ ID NO: 10 or a subsequence thereof.

In several embodiments, a probe capable of hybridizing to a *D. gatoi* nucleic molecule contains a nucleic acid sequence that is at least 95% identical, such as at least 96%, at least 97%, at least 98%, at least 99%, or even 100% identical, to the nucleotide sequence set forth as one of SEQ ID NO: 1, or SEQ ID NO: 2. In several embodiments, a primer capable of hybridizing to and directing the amplification of a *D. gatoi* nucleic acid molecule consists essentially of a nucleic acid sequence set forth as SEQ ID NO: 1 or SEQ ID NO: 2.

In several embodiments, a probe capable of hybridizing to a *D. cati* or nucleic molecule contains a nucleic acid sequence that is at least 95% identical, such as at least 96%, at least 97%, at least 98%, at least 99%, or even 100% identical, to the nucleotide sequence set forth as one of SEQ ID NO: 4, or SEQ ID NO: 5. In several embodiments, a primer capable of hybridizing to and directing the amplification of a *D. cati* nucleic acid molecule consists essentially of a nucleic acid sequence set forth as SEQ ID NO: 4 or SEQ ID NO: 5.

In some embodiments, the primer is detectably labeled, either with an isotopic or non-isotopic label, alternatively the target nucleic acid (such as a *D. gatoi* and/or *D. cati*) is labeled. Non-isotopic labels can include a fluorescent or luminescent molecule, biotin, an enzyme or enzyme substrate or a chemical.

In certain embodiments, the primers are a set of primers, such as a pair of primers, capable of hybridizing to and amplifying a *D. gatoi* and/or *D. cati* nucleic acid molecule. Such a set of primers includes at least one forward primer and a least one reverse primer, where the primers are specific for the amplification of a *D. gatoi* or a *D. cati* nucleic acid molecule. In some embodiments, the set of primers includes at least one pair of primers specific for the amplification a *D. gatoi* or *D. cati* n nucleic acid molecule, for example such a set of primers could include a pair of primers for the amplification of a *D. gatoi* nucleic acid molecule, a pair of primers for the amplification of *D. cati*, or any combination thereof, such as a pair of primers for the amplification of a *D. cati* nucleic acid molecule and a pair of primers for the amplification of a *D. gatoi* nucleic acid molecule.

In some examples, the set of primers includes a pair of primers that is specific for the amplification of a *D. gatoi* nucleic acid molecule that includes a portion of the nucleic acid sequence of *D. gatoi* ribosomal RNA gene, such as the nucleic acid sequence set forth as SEQ ID NO: 9. In certain examples, the pair of primers is specific for the amplification of a *D. gatoi* nucleic acid molecule and includes a forward primer at least 95% identical to SEQ ID NO: 1, such as at least 96%, at least 97%, at least 98%, at least 99%, or even 100% identical to SEQ ID NO: 1, and a reverse primer at least 95% identical to SEQ ID NO: 2, such as at least 96%, at least 97%, at least 98%, at least 99%, or even 100% identical to SEQ ID NO: 2.

In some examples, the set of primers includes a pair of primers that is specific for the amplification of a *D. cati* nucleic acid molecule that includes a portion of the nucleic acid sequence of the *D. cati* ribosomal RNA gene, such as the nucleic acid sequence set forth as SEQ ID NO: 10. In certain examples, the pair of primers is specific for the amplification of a *D. cati* nucleic acid molecule and includes a forward primer at least 95% identical to SEQ ID NO: 4, such as at least 96%, at least 97%, at least 98%, at least 99%, or even 100% identical to SEQ ID NO: 4, and a reverse primer at least 95% identical to SEQ ID NO: 5, such as at least 96%, at least 97%, at least 98%, at least 99%, or even 100% identical to SEQ ID NO: 5.

Although exemplary probes and primers are provided in SEQ ID NOs: 1-6, the primer and/or probe sequence can be varied slightly by moving the probes a few nucleotides upstream or downstream from the nucleotide positions that they hybridize to on the *D. gatoi* or *D. cati* nucleic molecule acid, provided that the probe and/or primer is still specific for the *D. gatoi* or *D. cati* nucleic acid sequence, for example specific for SEQ ID NO: 9, SEQ ID NO: 10. For example, variations of the probes and primers disclosed as SEQ ID NOs: 1-6 can be made by "sliding" the probes and/or primers a few nucleotides 5' or 3' from their positions, and that such variation will still be specific for *D. gatoi* or *D. cati*.

Also provided by the present application are probes and primers that include variations to the nucleotide sequences shown in any of SEQ ID NOs: 1-6, as long as such variations permit detection of the *D. gatoi* or *D. cati* nucleic acid molecule. For example, a probe or primer can have at least 95% sequence identity such as at least 96%, at least 97%, at least 98%, at least 99% to a nucleic acid consisting of the sequence shown in any of SEQ ID NOs: 1-6. In such examples, the number of nucleotides does not change, but the nucleic acid sequence shown in any of SEQ ID NOs: 1-6 can vary at a few nucleotides, such as changes at 1, 2, 3, or 4 nucleotides.

The present application also provides probes and primers that are slightly longer or shorter than the nucleotide sequences shown in any of SEQ ID NOs: 1-6, as long as such deletions or additions permit detection of the desired *D. gatoi* or *D. cati* nucleic acid molecule. For example, a probe can include a few nucleotide deletions or additions at the 5'- or 3'-end of the probe or primers shown in any of SEQ ID NOs: 1-6, such as addition or deletion of 1, 2, 3, or 4 nucleotides from the 5'- or 3'-end, or combinations thereof (such as a deletion from one end and an addition to the other end). In such examples, the number of nucleotides changes.

Detection of *D. gatoi* and *D. cati*

A major application of the *D. gatoi* and *D. cati* specific primers and probes disclosed herein is for the detection of *D. gatoi* and/or *D. cati* in a sample, such as a biological sample obtained from a subject that has or is suspected of having an *D. gatoi* and/or *D. cati* infection. Thus, the disclosed methods can be used to diagnose if a subject has *D. gatoi* and/or *D. cati*. Accordingly, methods for the detection of *D. gatoi* and/or *D. cati* nucleic acids are disclosed, for example to determine if a subject is infected with *D. gatoi* and/or *D. cati*. By using *D. gatoi* and/or *D. cati* probes can be used to detect the presence of and discriminate between *D. gatoi* and *D. cati* in a sample.

The methods described herein may be used for any purpose for which detection of *D. gatoi* and/or *D. cati* is desirable, including diagnostic and prognostic applications, such as in laboratory and clinical settings. Appropriate samples include any conventional environmental or biological samples, including clinical samples obtained from a veterinary subject.

Detecting a *D. gatoi* and/or *D. cati* nucleic acid in a sample involves contacting the sample with at least one of the *D. gatoi* or *D. cati* specific probes disclosed herein that is capable of hybridizing to a *D. gatoi* or *D. cati* nucleic acid, such as a *D. gatoi* or *D. cati* nucleic acid, under conditions of very high stringency (such as a nucleic acid probe capable of hybridizing under very high stringency conditions to a *D. gatoi* or *D. cati* nucleic acid sequence set forth as SEQ ID NO: 9, or SEQ ID NO: 10, for example a nucleic acid sequence at least 95% identical to the nucleotide sequence set forth as one of SEQ ID NO: 3, or SEQ ID NO: 6, such as a nucleic acid sequence consisting substantially of the nucleic acid sequence set forth as one of SEQ ID NO: 3, or SEQ ID NO:6), and detecting hybridization between the *D. gatoi* or *D. cati* nucleic acid and the probe. Detection of hybridization between the probe and the *D. gatoi* or *D. cati* nucleic acid indicates the presence of the *D. gatoi* or *D. cati* nucleic acid in the sample.

In some embodiments, *D. gatoi* or *D. cati* nucleic acids present in a sample are amplified prior to using a hybridization probe for detection. For instance, it can be advantageous to amplify a portion of the *D. gatoi* or *D. cati* nucleic acid, and then detect the presence of the amplified *D. gatoi* or *D. cati* nucleic acid.

Detecting the amplified product typically includes the use of labeled probes that are sufficiently complementary and hybridize to the amplified *D. gatoi* or *D. cati* nucleic acid sequence. Thus, the presence, amount, and/or identity of the amplified product can be detected by hybridizing a labeled probe, such as a fluorescently labeled probe, complementary to the amplified product. In one embodiment, the detection of a target nucleic acid sequence of interest, such as a *D. gatoi* or *D. cati* nucleic acid includes the combined use of PCR amplification and a labeled probe such that the product is measured using real-time PCR. In another embodiment, the detection of an amplified target nucleic acid sequence of interest includes the transfer of the amplified target nucleic acid to a solid support, such as a blot, for example a Northern blot, and probing the blot with a probe, for example a labeled probe, that is complementary to the amplified target nucleic acid sequence. In yet another embodiment, the detection of an amplified target nucleic acid sequence of interest includes the hybridization of a labeled amplified target nucleic acid to probes disclosed herein that are arrayed in a predetermined array with an addressable location and that are complementary to the amplified target nucleic acid.

Any nucleic acid amplification method can be used to detect the presence of *D. gatoi* and *D. cati* in a sample. In one specific, non-limiting example, polymerase chain reaction (PCR) is used to amplify the *D. gatoi* or *D. cati* nucleic acid sequences. In other specific, non-limiting examples, real-time PCR, reverse transcriptase-polymerase chain reaction (RT-PCR), real-time reverse transcriptase-polymerase chain reaction (rt RT-PCR), ligase chain reaction, or transcription-mediated amplification (TMA) is used to amplify the *D. gatoi* or *D. cati* nucleic acid. In a specific example, the *D. gatoi* or *D. cati* nucleic acid is amplified by real-time PCR, for example real-time TAQMAN® PCR. Techniques for nucleic acid amplification are well-known to those of skill in the art.

Typically, at least two primers are utilized in the amplification reaction, Amplification of the *D. gatoi* or *D. cati* nucleic acid involves contacting the *D. gatoi* or *D. cati* nucleic acid with one or more primers that are capable of hybridizing to and directing the amplification of a *D. gatoi* or *D. cati* nucleic acid (such as a primer capable of hybridizing under very high stringency conditions to *D. gatoi* or *D. cati* nucleic acid sequence set forth as SEQ NO: 9, or SEQ ID NO: 10, respectively, for example a primer that is least 95% identical (such as 100% identical) to the nucleotide sequence set forth as one of SEQ ID NO: 1, SEQ ID NO: 2, SEQ ID NO: 4, or SEQ ID NO: 5).

In some embodiments, the sample is contacted with a pair of primers that include a forward and reverse primer that both hybridize to a *D. gatoi* nucleic acid, such as a primer that is least 95% identical (such as 100% identical) to the nucleotide sequence set forth as SEQ ID NO: 1 and a primer that is least 95% identical (such as 100% identical) to the nucleotide sequence set forth as SEQ ID NO: 2. In some embodiments, the sample is contacted with a pair of primers that include a forward and reverse primer that both hybridize to a *D. cati* nucleic acid, such as a primer that is least 95% identical (such as 100% identical) to the nucleotide sequence set forth as SEQ ID NO: 4 and a primer that is least 95% identical (such as 100% identical) to the nucleotide sequence set forth as SEQ ID NO: 5.

The amplified *D. gatoi* or *D. cati* nucleic acid, can be detected in real-time, for example by real-time PCR, in order to determine the presence, and/or the amount of *D. gatoi* or *D. cati* specific nucleic acid in a sample. In this manner, an amplified nucleic acid sequence, such as an amplified *D. gatoi* or *D. cati* nucleic acid sequence, can be detected using a probe specific for the product amplified from the *D. gatoi* or *D. cati* sequence of interest.

Real-time PCR monitors the fluorescence emitted during the reaction as an indicator of amplicon production during each PCR cycle as opposed to the endpoint detection. The real-time progress of the reaction can be viewed in some systems. Typically, real-time PCR uses the detection of a fluorescent reporter. Typically, the fluorescent reporter's signal increases in direct proportion to the amount of PCR product in a reaction. By recording the amount of fluorescence emission at each cycle, it is possible to monitor the PCR reaction during exponential phase where the first significant increase in the amount of PCR product correlates to the initial amount of target template. The higher the starting copy number of the nucleic acid target, the sooner a significant increase in fluorescence is observed.

In one embodiment, the fluorescently-labeled probes rely upon fluorescence resonance energy transfer (FRET), or in a change in the fluorescence emission wavelength of a sample, as a method to detect hybridization of a DNA probe to the amplified target nucleic acid in real-time. For example, FRET that occurs between fluorogenic labels on different probes (for example, using HybProbes) or between a fluorophore and a non-fluorescent quencher on the same probe (for example, using a molecular beacon or a TAQMAN® probe) can identify a probe that specifically hybridizes to the DNA sequence of interest and in this way, using a *D. gatoi* or *D. cati* probe, can detect the presence, and/or amount of *D. gatoi* or *D. cati* in a sample. In some embodiments, the fluorescently-labeled DNA probes used to identify amplification products have spectrally distinct emission wavelengths, thus allowing them to be distinguished within the same reaction tube, for example in multiplex PCR, for example a multiplex real-time PCR. In some embodiments, the probes and primers disclosed herein are used in multiplex real-time PCR. For example, multiplex PCR permits the simultaneous detection of the amplification products of a *D. gatoi* and *D. cati* nucleic acid using the disclosed probes or even an other nucleic acid, such as a control nucleic acid.

In another embodiment, a melting curve analysis of the amplified target nucleic acid can be performed subsequent to the amplification process. The $T_m$ of a nucleic acid sequence depends on the length of the sequence and its G/C content. Thus, the identification of the $T_m$ for a nucleic acid sequence can be used to identify the amplified nucleic acid, for example by using double-stranded DNA binding dye chemistry, which quantitates the amplicon production by the use of a non-sequence specific fluorescent intercalating agent (such as SYBR-green or ethidium bromide). SYBR green is a fluorogenic minor groove binding dye that exhibits little fluorescence when in solution but emits a strong fluorescent signal upon binding to double-stranded DNA. Typically, SYBR green is used in singleplex reactions, however when coupled with melting point analysis, it can be used for multiplex reactions.

Any type of thermal cycler apparatus can be used for the amplification of the *D. gatoi* and/or *D. cati* nucleic acid and/or the determination of hybridization. Examples of suitable apparatuses include a PTC-100® Peltier Thermal Cycler (MJ Research, Inc.; San Francisco, Calif.), a ROBOCYCLER® 40 Temperature Cycler (Stratagene; La Jolla, Calif.), or a GENEAMP® PCR System 9700 (Applied Biosystems; Foster City, Calif.). For real-time PCR, any type of real-time thermocycler apparatus can be used. For example, a BioRad iCycler iQ™, LIGHTCYCLER™ (Roche; Mannheim, Germany), a 7700 Sequence Detector (Perkin Elmer/Applied Biosystems; Foster City, Calif.), ABI™ systems such as the 7000, 7500, 7700, or 7900 systems (Applied Biosystems; Foster City, Calif.), or an MX4000™, MX3000™ or MX3005™ (Stratagene; La Jolla, Calif.); DNA Engine Opticon Continuous Fluorescence Detection System (MJ Research); and Cepheid SMARTCYCLER™ can by used to amplify nucleic acid sequences in real-time.

In some embodiments, detecting the presence of a *D. gatoi* or *D. cati* nucleic acid sequence in a sample includes the extraction of *D. gatoi* or *D. cati* DNA. DNA extraction relates to releasing DNA from a latent or inaccessible form in a cell or sample and allowing the DNA to become freely available. In such a state, it is suitable for effective detection and/or amplification of the *D. gatoi* or *D. cati* nucleic acid. Releasing DNA may include steps that achieve the disruption of cells. Additionally, extraction of DNA may include steps that achieve at least a partial separation of the RNA dissolved in an aqueous medium from other cellular components, wherein such components may be either particulate or dissolved.

In some embodiments, detecting the presence of a *D. gatoi* or *D. cati* nucleic acid sequence in a sample includes the extraction of *D. gatoi* and *D. cati* RNA. RNA extraction relates to releasing RNA from a latent or inaccessible form in a cell or sample and allowing the RNA to become freely available. In such a state, it is suitable for effective detection and/or amplification of the *D. gatoi* or *D. cati* nucleic acid. Releasing RNA may include steps that achieve the disruption of cells. Extraction of RNA is generally carried out under conditions that effectively exclude or inhibit any ribonuclease activity that may be present. Additionally, extraction of RNA may include steps that achieve at least a partial separation of the RNA dissolved in an aqueous medium from other cellular components, wherein such components may be either particulate or dissolved.

One of ordinary skill in the art will know suitable methods for extracting nucleic acids such as RNA and/or DNA from a sample; such methods will depend upon, for example, the type of sample in which the *D. gatoi* or *D. cati* nucleic acid is found. For example, the nucleic acids may be extracted using guanidinium isothiocyanate, such as the single-step isolation by acid guanidinium isothiocyanate-phenol-chloroform extraction of Chomczynski et al. (*Anal. Biochem.* 162:156-59, 1987). The sample can be used directly or can be processed, such as by adding solvents, preservatives, buffers, or other compounds or substances. Nucleic acids can be extracted using standard methods. For instance, rapid nucleic acid preparation can be performed using a commercially available kit (such as the QIAGEN® DNA Mini kit (QIAGEN®) Roche MagNA Pure Compact Nucleic Acid Isolation Kit I or RNEASY® Mini Kit (QIAGEN®); NUCLISENS® NASBA Diagnostics (bioMérieux); or the MASTERPURE™ Complete DNA and RNA Purification Kit (EPICENTRE)).

In some embodiments, the probe and/or primer is detectably labeled, either with an isotopic or non-isotopic label; in alternative embodiments, the *D. gatoi* or *D. cati* nucleic acid is labeled. Non-isotopic labels can, for instance, comprise a fluorescent or luminescent molecule, or an enzyme, co-factor, enzyme substrate, or hapten. The probe is incubated with a single-stranded or double-stranded preparation of RNA, DNA, or a mixture of both, and hybridization determined. In some examples, the hybridization results in a detectable change in signal such as in increase or decrease in signal, for example from the labeled probe. Thus, detecting hybridization comprises detecting a change in signal from the labeled probe during or after hybridization relative to signal from the label before hybridization.

*D. gatoi* and/or *D. cati* Identification Arrays

An array containing a plurality of heterogeneous probes for the detection, of *D. gatoi* and/or *D. cati* are disclosed. Such arrays may be used to rapidly detect *D. gatoi* and/or *D. cati* in a sample.

Arrays are arrangements of addressable locations on a substrate, with each address containing a nucleic acid, such as a probe, such as a *D. gatoi* and/or *D. cati* probe as disclosed herein. In some embodiments, each address corresponds to a single type or class of nucleic acid, such as a single probe, though a particular nucleic acid may be redundantly contained at multiple addresses. A "microarray" is a miniaturized array requiring microscopic examination for detection of hybridization. Larger "macroarrays" allow each address to be recognizable by the naked human eye and, in some embodiments, a hybridization signal is detectable without additional magnification. The addresses may be labeled, keyed to a separate guide, or otherwise identified by location.

In some embodiments, a *D. gatoi* and/or *D. cati* detection array is a collection of separate probes at the array addresses. The *D. gatoi* and/or *D. cati* detection array is then contacted with a sample suspected of containing *D. gatoi* and/or *D. cati* nucleic acids under conditions allowing hybridization between the probe and nucleic acids in the sample to occur. Any sample potentially containing, or even suspected of containing *D. gatoi* and/or *D. cati* nucleic acids may be used, including nucleic acid extracts, such as amplified or non-amplified DNA or RNA preparations. A hybridization signal from an individual address on the array indicates that the probe hybridizes to a nucleotide within the sample. This system permits the simultaneous analysis of a sample by plural probes and yields information identifying the *D. gatoi* and/or *D. cati* nucleic acids contained within the sample. In alternative embodiments, the array contains *D. gatoi* and/or *D. cati* nucleic acids and the array is contacted with a sample containing a probe. In any such embodiment, either the probe or the *D. gatoi* and/or *D. cati* nucleic acids may be labeled to facilitate detection of hybridization.

The nucleic acids may be added to an array substrate in dry or liquid form. Other compounds or substances may be added to the array as well, such as buffers, stabilizers, reagents for detecting hybridization signal, emulsifying agents, or preservatives.

In certain examples, the array includes one or more molecules or samples occurring on the array a plurality of times (twice or more) to provide an added feature to the array, such as redundant activity or to provide internal controls.

Within an array, each arrayed nucleic acid is addressable, such that its location may be reliably and consistently determined within the at least the two dimensions of the array surface. Thus, ordered arrays allow assignment of the location of each nucleic acid at the time it is placed within the array. Usually, an array map or key is provided to correlate each address with the appropriate nucleic acid. Ordered arrays are often arranged in a symmetrical grid pattern, but nucleic acids could be arranged in other patterns (for example, in radially distributed lines, a "spokes and wheel" pattern, or ordered clusters). Addressable arrays can be computer readable; a computer can be programmed to correlate a particular address on the array with information about the sample at that position, such as hybridization or binding data, including signal intensity. In some exemplary computer readable formats, the individual samples or molecules in the array are arranged regularly (for example, in a Cartesian grid pattern), which can be correlated to address information by a computer.

An address within the array may be of any suitable shape and size. In some embodiments, the nucleic acids are suspended in a liquid medium and contained within square or rectangular wells on the array substrate. However, the nucleic acids may be contained in regions that are essentially triangular, oval, circular, or irregular. The overall shape of the array itself also may vary, though in some embodiments it is substantially flat and rectangular or square in shape.

*D. gatoi* and/or *D. cati* detection arrays may vary in structure, composition, and intended functionality, and may be based on either a macroarray or a microarray format, or a combination thereof. Such arrays can include, for example, at least 10, at least 25, at least 50, at least 100, or more addresses, usually with a single type of nucleic acid at each address. In the case of macroarrays, sophisticated equipment is usually not required to detect a hybridization signal on the array, though quantification may be assisted by standard scanning and/or quantification techniques and equipment. Thus, macroarray analysis as described herein can be carried out in most hospitals, agricultural and medial research laboratories, universities, or other institutions without the need for investment in specialized and expensive reading equipment.

Examples of substrates for the arrays disclosed herein include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (for example glass or a supported membrane) or flexible (such as a polymer membrane). One commercially available product line suitable for probe arrays described herein is the Microlite line of MICROTITER® plates available from Dynex Technologies UK (Middlesex, United Kingdom), such as the Microlite 1+ 96-well plate, or the 384 Microlite+ 384-well plate.

Addresses on the array should be discrete, in that hybridization signals from individual addresses can be distinguished from signals of neighboring addresses, either by the naked eye (macroarrays) or by scanning or reading by a piece of equipment or with the assistance of a microscope (microarrays).

Addresses in an array may be of a relatively large size, such as large enough to permit detection of a hybridization signal without the assistance of a microscope or other equipment. Thus, addresses may be as small as about 0.1 mm across, with a separation of about the same distance. Alternatively, addresses may be about 0.5, 1, 2, 3, 5, 7, or 10 mm across, with a separation of a similar or different distance. Larger addresses (larger than 10 mm across) are employed in certain embodiments. The overall size of the array is generally correlated with size of the addresses (for example, larger addresses will usually be found on larger arrays, while smaller addresses may be found on smaller arrays). Such a correlation is not necessary, however.

The arrays herein may be described by their densities (the number of addresses in a certain specified surface area). For macroarrays, array density may be about one address per square decimeter (or one address in a 10 cm by 10 cm region of the array substrate) to about 50 addresses per square centimeter (50 targets within a 1 cm by 1 cm region of the substrate). For microarrays, array density will usually be one or more addresses per square centimeter, for instance, about 50, about 100, about 200, about 300, about 400, about 500, about 1000, about 1500, about 2,500, or more addresses per square centimeter.

The use of the term "array" includes the arrays found in DNA microchip technology. As one, non-limiting example, the probes could be contained on a DNA microchip similar to the GENECHIP® products and related products commercially available from Affymetrix, Inc. (Santa Clara, Calif.). Briefly, a DNA microchip is a miniaturized, high-density array of probes on a glass wafer substrate. Particular probes are selected, and photolithographic masks are designed for use in a process based on solid-phase chemical synthesis and photolithographic fabrication techniques similar to those used in the semiconductor industry. The masks are used to isolate chip exposure sites, and probes are chemically synthesized at these sites, with each probe in an identified location within the array. After fabrication, the array is ready for hybridization. The probe or the nucleic acid within the sample may be labeled, such as with a fluorescent label and, after hybridization, the hybridization signals may be detected and analyzed.

Kits

The nucleic acid primers and probes disclosed herein can be supplied in the form of a kit for use in the detection *D. gatoi* and/or *D. cati*, including kits for any of the arrays described above. In such a kit, an appropriate amount of one or more of the nucleic acid probes and/or primers is provided in one or more containers or held on a substrate. A nucleic acid probe and/or primer may be provided suspended in an aqueous solution or as a freeze-dried or lyophilized powder, for instance. The container(s) in which the nucleic acid(s) are supplied can be any conventional container that is capable of holding the supplied form, for instance, microfuge tubes, ampoules, or bottles. The kits can include either labeled or unlabeled nucleic acid probes for use in detection of *D. gatoi* and/or *D. cati* nucleotide sequences.

In some applications, one or more primers (as described above), such as pairs of primers, may be provided in pre-measured single use amounts in individual, typically disposable, tubes or equivalent containers. With such an arrangement, the sample to be tested for the presence of *D. gatoi* and/or *D. cati* nucleic acids can be added to the individual tubes and amplification carried out directly.

The amount of nucleic acid primer supplied in the kit can be any appropriate amount, and may depend on the target market to which the product is directed. For instance, if the kit is adapted for research or clinical use, the amount of each nucleic acid primer provided would likely be an amount sufficient to prime several PCR amplification reactions. General guidelines for determining appropriate amounts may be found in Innis et al., Sambrook et al., and Ausubel et al. A kit may include more than two primers in order to facilitate the PCR amplification of a larger number of *D. gatoi* and *D. cati* nucleotide sequences.

In some embodiments, kits also may include the reagents necessary to carry out PCR amplification reactions, including DNA sample preparation reagents, appropriate buffers (such as polymerase buffer), salts (for example, magnesium chloride), and deoxyribonucleotides (dNTPs).

Particular embodiments include a kit for detecting a *D. gatoi* and/or *D. cati* nucleic acid based on the arrays described above. Such a kit includes at least one probe specific for a *D. gatoi* and/or *D. cati* nucleic acid (as described above) and instructions. A kit may contain more than one different probe, such as 2, 3, 4, 5, 6, 7, 8, 9, 10, 11, 12, 13, 14, 15, 20, 25, 50, 100, or more probes. The instructions may include directions for obtaining a sample, processing the sample, preparing the probes, and/or contacting each probe with an aliquot of the sample. In certain embodiments, the kit includes an apparatus for separating the different probes, such as individual containers (for example, microtubules) or an array substrate (such as, a 96-well or 384-well microtiter plate). In particular embodiments, the kit includes prepackaged probes, such as probes suspended in suitable medium in individual containers (for example, individually sealed EPPENDORF® tubes) or the wells of an array substrate (for example, a 96-well microtiter plate sealed with a protective plastic film). In other particular embodiments, the kit includes equipment, reagents, and instructions for extracting and/or purifying nucleotides from a sample.

The following examples are provided to illustrate particular features of certain embodiments. However, the particular features described below should not be construed as limitations on the scope of the invention, but rather as examples from which equivalents will be recognized by those of ordinary skill in the art.

EXAMPLES

Example 1

Materials and Methods

This example describes the materials and methods used to determine the specificity and sensitivity of the disclosed probes and primers.

The goal of the current research was to develop a molecular diagnostic method to diagnose *D. gatoi* infection in cats and to distinguish these mites from *D. cati*. However, no nucleic acid sequence was available for either mite species. To accomplish this goal *D. gatoi* and *D. cati* was obtained from cat skin and putatively identified the mites based on morphological characteristics. DNA was extracted from the collected material using a commercial kit (DNeasy blood and tissue kit, Qiagen, Valencia, Calif.). PCR amplification was performed using primers FWD-ACTGTGCTAAGGTAGCGAAGTCA (SEQ ID NO: 7) and REV-TCAAAAGCCAACATCGAG (SEQ ID NO: 8) which we designed to amplify 16S rRNA DNA from demodectic mites. These primers were designed based on 16S rRNA gene sequences available in GenBank from mites infecting non-feline species including *Demodex canis* (JF784001, JF784000), *Demodex brevis* (JF783999, HQ844220, JF783998), and *Demodex folliculorum* (JF783996, JF783994). Sequences were aligned using multiple sequence alignment software (MegAlign, DNAstar, Madison, Wis.) and conserved areas identified. Candidate primers were produced using Primer3 software (Whitehead Institute for Biomedical Research). PCR reaction mixtures consisted of 2 µl of DNA template, 25 pmol of each primer, and 25 µl of premix rtaq 2×DNA polymerase mastermix (Takara Bio, Otsu, Shiga, Japan) containing 0.4 mmol/L of each deoxynucleoside triphosphate (dNTP) in a total volume of 50 µl. Parameters used for PCR amplification were 95° C. for 90 s followed by 35 cycles of 55° C. for 30 s, 68° C. for 120 s, and 94° C. for 30 s. A final cycle consisted of 55° C. for 30 s and 68° C. for 5 min. PCR products were resolved and visualized by electrophoresis in gels containing 1.4% agarose and 0.5 µg/ml ethidium bromide. Samples containing PCR products of expected sizes were sequenced. Sequences were aligned with related entries in public databases using the BLASTN algorithm with the National Center for Biotechnology Information (NCBI) online resource. Phylogenetic analysis was performed using MegAlign software. Quantitative PCR (qPCR) primers and probes were designed to amplify and detect *D. gatoi* using the 16S rRNA DNA sequence information obtained from this study as no other sequence data exists for this species of mite. qPCR for the detection of *D. gatoi* was performed with forward primer GACGAGAAGACCCTAGAATCTTTATTTTCA (SEQ ID NO: 1), reverse primer CCTAAATGATCTATCCTAC-CAACCTTAAAAAGTT (SEQ ID NO: 2) and FAM labeled TaqMan MGB probe AATATAAAACTTTC- CCCCAAATAAA (SEQ ID NO: 3) with nonfluorescent quencher (NFQ) synthesized by a commercial source (Applied Biosystems, Foster City, Calif.). A qPCR method was also developed for *D. cati* to identify cats infected with this mite or both mites. qPCR for the detection of *D. cati* was performed with forward primer TTCCATGAAAAATTG-GAATTATTTCTAAAGACGAG (SEQ ID NO: 4), reverse primer AAAATAAAACTTTCCCCCAAATAAAAAT-TAAAATACCTTT (SEQ ID NO: 5) and FAM labeled TaqMan MGB probe AAGACCCCGAAATCT (SEQ ID NO: 6) with NFQ. qPCR was performed with 20 µl total volume reactions containing 10 µl TaqMan® 2× Universal PCR Master Mix, No Amperase UNG (Applied Biosystems, Foster City, Calif.), 8 µl water, 1 µl template DNA, and 1 µl primer and probe mix (Applied Biosystems, Foster City, Calif.). Samples were placed in a 48-well plate and amplified using a StepOne™ Real-Time PCR System (Applied Biosystems, Foster City, Calif.). Thermal cycler parameters were as follows: 50° C. for 2 min, 95° C. for 10 min, 40 cycles: 95° C. for 15 s and 60° C. for 1 min. Ct values were calculated using StepOne software version 2.0.

Field testing was conducted on samples obtained from 75 cats including 52 from animal shelters. Among the cats two from the same shelter were identified as being pruritic. Samples included hair and skin swabs and DNA was isolated as described above.

Results/Discussion

Figure 2:
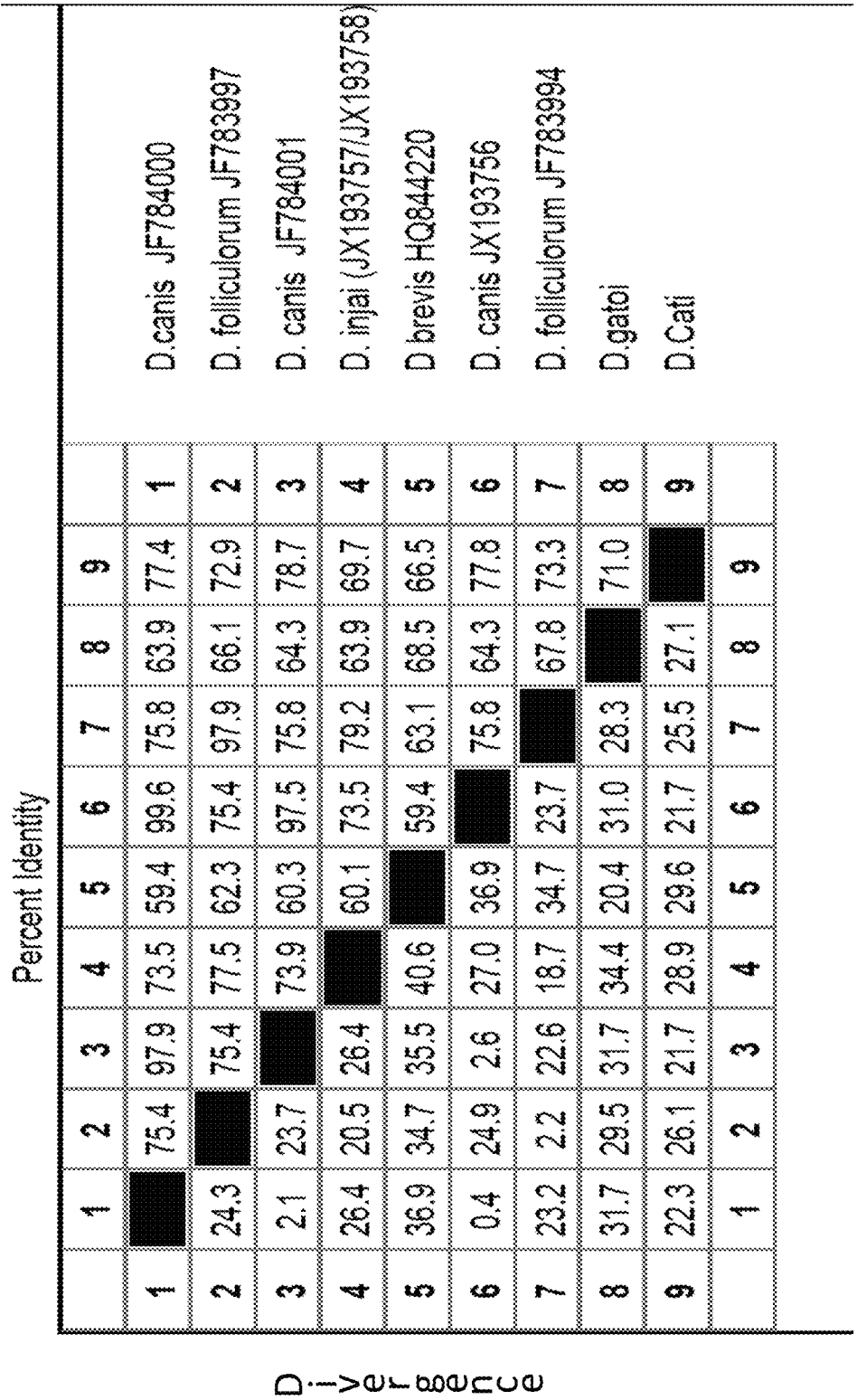
FIG. 2 is table showing the Identity of demodex rRNA gene sequences.
Figure 3:
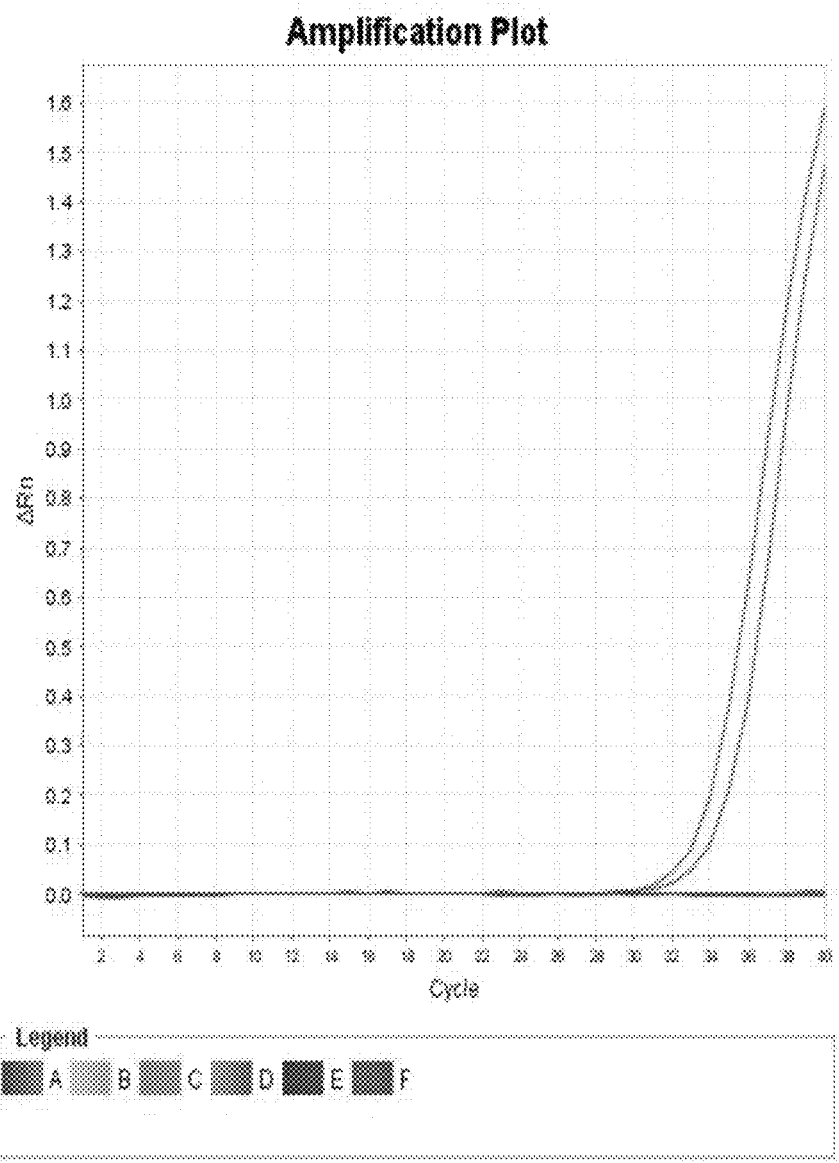
FIG. 3 is a graph of *D. gatoi* specific real-time PCR assay, showing the efficiency of the probe and primer sets.

DNA sequences were obtained for portions of the rRNA genes from *D. gatoi* (SEQ ID NO: 9) and *D. cati* (SEQ ID NO: 10) mites. They are not closely related to any DNA sequences in public databases and share approximately 71% identity with each other (FIGS. 1 and 2). qPCR with *D. gatoi* specific primers and probe specifically amplified DNA isolated from *D. gatoi* and did not produce a Ct value (was negative) with *D. cati* DNA. Conversely, the *D. cati* qPCR primers and probe produced a positive response with the *D. cati* DNA and did not produce a Ct value with *D. gatoi*.

Of the 75 cats tested by qPCR for *D. gatoi* DNA five were positive. All five were from the same shelter and either were pruritic or in close contact with a pruritic cat in a shelter. None of the *D. gatoi* samples were positive for *D. cati* and one cat was positive for *D. cati* and negative for *D. gatoi*.

This study is the first report of nucleic acid sequences from mites affecting cats. The sequences were used to establish novel tests for the identification and differentiation of *D. gatoi* and *D. cati*. Field testing demonstrates the usefulness of the test to detect *D. gatoi* on symptomatic cats and cats at risk of infection due to contact with infected cats. This test will provide a valuable and novel technique for the diagnosis of *D. gatoi* infection and may also be useful to monitor response to therapy and to assess the efficacy of products designed to prevent or treat infection.

While this disclosure has been described with an emphasis upon particular embodiments, it will be obvious to those of ordinary skill in the art that variations of the particular embodiments may be used, and it is intended that the disclosure may be practiced otherwise than as specifically described herein. Features, characteristics, compounds, chemical moieties, or examples described in conjunction with a particular aspect, embodiment, or example of the invention are to be understood to be applicable to any other aspect, embodiment, or example of the invention. Accordingly, this disclosure includes all modifications encompassed within the spirit and scope of the disclosure as defined by the following claims.

---

We claim:

1. A method for detecting a *Demodex gatoi* or *Demodex cati* nucleic acid in a sample, comprising:
   contacting the sample with at least one probe comprising a nucleic acid sequence between 15 and 50 nucleotides in length capable of hybridizing to a *Demodex gatoi* or *Demodex cati* nucleic acid sequence set forth as SEQ ID NO: 9, or SEQ ID NO: 10; and
   detecting hybridization between the *Demodex gatoi* or *Demodex cati* nucleic acid and the probe, wherein the detection of hybridization indicates the presence of the *Demodex gatoi* or *Demodex cati* nucleic acid in the sample.

2. The method of claim 1, wherein the probe comprises a nucleic acid sequence at least 95% identical to the nucleotide sequence set forth as SEQ ID NO: 3 or SEQ ID NO: 6.

3. The method according to claim 1, wherein the probe is labeled.

4. The method according to claim 3, wherein detecting hybridization comprises detecting a change in signal from the labeled probe during or after hybridization relative to signal from the label before hybridization.

5. The method according to claim 1, wherein the method discriminates between a *Demodex gatoi* nucleic acid and a *Demodex cati* nucleic acid.

6. The method according to claim 1, further comprising amplifying the *Demodex gatoi* or *Demodex cati* nucleic acid by polymerase chain reaction (PCR), real-time PCR, reverse transcriptase-polymerase chain reaction (RT-PCR), real-time reverse transcriptase-polymerase chain reaction (rt RT-PCR), ligase chain reaction, or transcription-mediated amplification (TMA).

7. The method according to claim 6, wherein the *Demodex gatoi* or *Demodex cati* nucleic acid is amplified by real-time PCR.

8. The method according to claim 6, wherein amplifying the *Demodex gatoi* or *Demodex cati* nucleic acid comprises contacting the sample with at least one primer between 15 and 40 nucleotides in length capable of hybridizing to a *Demodex gatoi* or *Demodex cati* nucleic acid sequence set forth as SEQ ID NO: 9 or SEQ ID NO: 10, wherein the primer is capable of amplifying the *Demodex gatoi* or *Demodex cati* nucleic acid.

9. The method according to claim 8, wherein the primer comprises a nucleic acid sequence at least 95% identical to the nucleotide sequence set forth as SEQ ID NO: 1, SEQ ID NO: 2, SEQ ID NO: 4, or SEQ ID NO: 5.

10. The method according to claim 1, wherein the sample is a biological sample obtained from a subject.

11. The method of claim 10, wherein the presence of a *Demodex gatoi* or *Demodex cati* acid in the biological sample indicates the presence of *Demodex gatoi* or *Demodex cati* infection in the biological sample obtained from a subject.

12. The method according to claim 1, wherein the probe is arrayed in a predetermined array with an addressable location.

* * * * *

SEQUENCE LISTING

```
<160> NUMBER OF SEQ ID NOS: 10

<210> SEQ ID NO 1
<211> LENGTH: 30
<212> TYPE: DNA
<213> ORGANISM: Demodex gatoi

<400> SEQUENCE: 1
gacgagaaga ccctagaatc tttattttca                              30

<210> SEQ ID NO 2
<211> LENGTH: 34
<212> TYPE: DNA
<213> ORGANISM: Demodex gatoi

<400> SEQUENCE: 2
cctaaatgat ctatcctacc aaccttaaaa agtt                         34

<210> SEQ ID NO 3
<211> LENGTH: 25
<212> TYPE: DNA
<213> ORGANISM: Demodex gatoi

<400> SEQUENCE: 3
aatataaaac tttcccccaa ataaa                                   25

<210> SEQ ID NO 4
<211> LENGTH: 35
<212> TYPE: DNA
```

<213> ORGANISM: Demodex cati

<400> SEQUENCE: 4
ttccatgaaa aatggaatt atttctaaag acgag                                35

<210> SEQ ID NO 5
<211> LENGTH: 40
<212> TYPE: DNA
<213> ORGANISM: Demodex cati

<400> SEQUENCE: 5
aaaataaaac tttcccccaa ataaaaatta aaataccttt                          40

<210> SEQ ID NO 6
<211> LENGTH: 15
<212> TYPE: DNA
<213> ORGANISM: Demodex cati

<400> SEQUENCE: 6
aagaccccga aatct                                                     15

<210> SEQ ID NO 7
<211> LENGTH: 23
<212> TYPE: DNA
<213> ORGANISM: Demodex gatoi

<400> SEQUENCE: 7
actgtgctaa ggtagcgaag tca                                            23

<210> SEQ ID NO 8
<211> LENGTH: 18
<212> TYPE: DNA
<213> ORGANISM: Demodex gatoi

<400> SEQUENCE: 8
tcaaaagcca acatcgag                                                  18

<210> SEQ ID NO 9
<211> LENGTH: 330
<212> TYPE: DNA
<213> ORGANISM: Demodex gatoi

<400> SEQUENCE: 9
tactgtgcta aggtagcgaa gtcatttgtt tttttattgg aaacttgtat gagggatt      60
atggagtaga ttatttgaaa attttatatt taggaatttg atatttggat gaaaatttct   120
aattttctt aaagacgaga agaccctaga atctttattt tcataattag ggtgaatttt    180
tatttgggg aaagttttat atttataaaa agatttgtta ttttgaactt tttaaggttg    240
gtaggataga tactttaggg ataacaggat aattttcttt tgaagttctt attttggagg   300
aagtttatta cctcgatgtt ggcttttgaa                                    330

<210> SEQ ID NO 10
<211> LENGTH: 302
<212> TYPE: DNA
<213> ORGANISM: Demodex cati

<400> SEQUENCE: 10
ctcytgggaa ataaggaact tcaaagaaaa taatcctgtt aaccccgaag tatctatcca    60
atcaacctac aaaagttcct cataataaaa ataaatataa aaataaaact ttcccccaaa   120
taaaaattaa aataccttt tctaaaataa agatttcggg gtcttctcgt ctttagaaat    180

```
aattccaatt tttcatggaa aaattaaatt caccaattaa aacattcata aaaaaatctt    240
cattaatccc ctcatacaag tttccaataa aaaaacaaat gacttcgcta ccttagcaca    300
gt                                                                  302
```